United States Patent
Kogure et al.

(10) Patent No.: US 6,456,943 B1
(45) Date of Patent: Sep. 24, 2002

(54) CARBON DIOXIDE CONCENTRATION SENSOR

(75) Inventors: Shinsuke Kogure; Shinichi Yonemura, both of Tokyo (JP)

(73) Assignee: Riken Keiki Co., Ltd., Tokyo (JP)

( * ) Notice: Subject to any disclaimer, the term of this patent is extended or adjusted under 35 U.S.C. 154(b) by 0 days.

(21) Appl. No.: 09/311,578

(22) Filed: May 14, 1999

(30) Foreign Application Priority Data

May 15, 1998 (JP) .......................................... 10-132930

(51) Int. Cl.[7] .................................................. B60H 1/00
(52) U.S. Cl. .......................... 702/23; 702/24; 702/27; 702/30; 702/50; 702/85; 702/104
(58) Field of Search .............................. 702/22, 23, 24, 702/27, 30–32, 50, 85, 104, 107, 116, 127, 176, 178, 179, 181, 182, 183, 188, 189, FOR 103, FOR 104, FOR 115–119, FOR 127–128, FOR 134–135, FOR 139, FOR 156, FOR 154, FOR 159–160, FOR 170–171; 204/401, 406; 73/1.02, 1.06, 1.03, 1.07, 23.2, 23.31, 24.02

(56) References Cited

U.S. PATENT DOCUMENTS

| | | | | |
|---|---|---|---|---|
| 4,437,391 A | * | 3/1984 | Eguchi et al. ................ 98/2.01 |
| 4,658,790 A | * | 4/1987 | Kitahara ...................... 123/440 |
| 4,958,513 A | * | 9/1990 | Yasunage et al. ............. 73/23.2 |
| 5,421,981 A | * | 6/1995 | Leader et al. ................ 204/409 |
| 5,533,512 A | * | 7/1996 | Novotny et al. ............. 128/719 |
| 5,872,721 A | * | 2/1999 | Huston et al. ............... 364/510 |
| 5,886,247 A | * | 3/1999 | Rabbett ....................... 73/23.2 |
| 5,948,965 A | * | 9/1999 | Upchurch et al. .......... 73/23.31 |
| 6,061,637 A | * | 5/2000 | Sorge et al. ................... 702/24 |
| 6,076,392 A | * | 6/2000 | Drzewiecki .................. 73/23.2 |
| 6,082,176 A | * | 7/2000 | Kondo et al. ............... 73/23.31 |
| 6,092,430 A | * | 7/2000 | Liston et al. ............. 73/863.81 |
| 6,110,038 A | * | 8/2000 | Stern ........................... 454/343 |

* cited by examiner

Primary Examiner—Marc S. Hoff
Assistant Examiner—Carol S Tsai
(74) Attorney, Agent, or Firm—Connolly Bove Lodge & Hutz, LLP; Larry J. Hume

(57) ABSTRACT

A carbon dioxide sensor has an arithmetic unit 12 that predicts the minimum value of carbon dioxide concentration that is regulated by the diffusion of the atmosphere by judging that a signal from a carbon dioxide concentration sensing unit 1 indicates a declining tendency and a calibration unit 13 that updates the sensitivity correction factor based on the predicted minimum value. This permits quick calibration by eliminating the need to wait until the carbon dioxide concentration in any given environment reaches the minimum value.

17 Claims, 3 Drawing Sheets

CARBON DIOXIDE CONCENTRATION SENSOR

FIELD OF THE INVENTION

This invention relates to carbon dioxide concentration sensors that determine the concentration of carbon dioxide in a given environment while carrying out calibration based on the carbon dioxide concentration in the reference atmosphere.

DESCRIPTION OF THE PRIOR ART

Outputs from carbon dioxide sensors employing solid electrolytes or infrared rays vary with time. Therefore, such sensors correct their sensitivity by using calibration data prepared by statistically processing the chronologically measured and stored carbon dioxide concentrations in the reference air, as described in Japanese Provisional Patent Publication No. 249073 of 1993.

This type of sensors permit correction of changes in the carbon dioxide sensing means with age if the concentration of carbon dioxide in the environment has lowered to the level of carbon dioxide in the reference air. In modern offices and other similar extremely airtight buildings, however, accurate calibration is practically difficult to achieve because it takes a very long time for the carbon dioxide concentration to reach the minimum value.

SUMMARY OF THE INVENTION

A carbon dioxide sensor of this invention comprises a carbon dioxide sensing unit, an arithmetic unit that predicts the minimum value of carbon dioxide concentration that is regulated by the diffusion of the atmosphere by checking if the signal from a carbon dioxide sensing unit indicates that the carbon dioxide concentration has entered the declining phase, and a calibrating unit that updates the sensitivity correction factor based on the predicted lowest carbon dioxide concentration.

When the carbon dioxide in the environment is decreasing, its concentration is regulated by diffusion equation etc. and changes substantially univocally. Thus, the sensor according to this invention can predict with accuracy the minimum value of carbon dioxide concentration. Therefore, calibration can be made without waiting until the carbon dioxide concentration actually drops to the minimum value.

The object of this invention is to provide carbon dioxide concentration sensors that permit correcting sensitivity, zero point, and other calibration factors without waiting until the carbon dioxide concentration in the environment reaches the minimum value.

DESCRIPTION OF PREFERRED EMBODIMENTS

Figure 1:
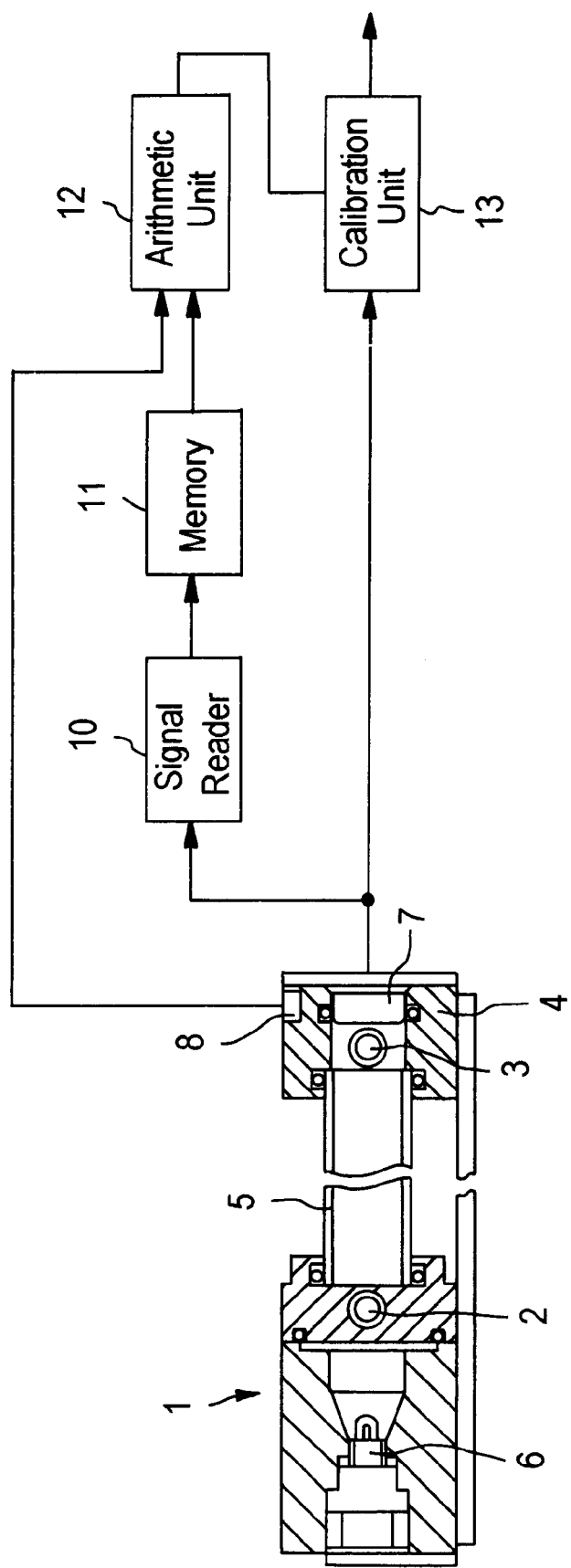
FIG. 1 is a block diagram of a carbon dioxide concentration sensor according to this invention.

FIG. 1 shows a carbon dioxide concentration sensor according to this invention, which comprises a carbon dioxide sensing unit. A non-dispersive infrared sensor 1 serving as the carbon dioxide sensing unit in this embodiment comprises a chamber 5 fastened to a base 4 having a gas inlet 2 and a gas outlet 3 at both ends thereof, an infrared-ray emitter 6, such as an incandescent lamp used here, on one side of the chamber, an infrared-ray sensor 7, such as a pyroelectric infrared ray sensor used here, and, if required, a temperature sensor 8.

A signal fetching unit 10 fetches signals from the infrared-ray sensor 7 into a memory 11 at given intervals, such as at intervals of 10 minutes. An arithmetic unit 12 is configured to arithmetically predict the minimum value of carbon dioxide in the environment in which no person is present based on the signals stored in the memory when the carbon dioxide concentration in the environment shows a tendency to drop at preset times, or under predetermined conditions when no person is present such as during the nighttime or on holidays.

A calibration unit 13 updates the sensitivity correction factor by using the value calculated by the arithmetic unit as the reference value, corrects the signal based on the updated sensitivity correction factor, and outputs the obtained result.

Figure 2:
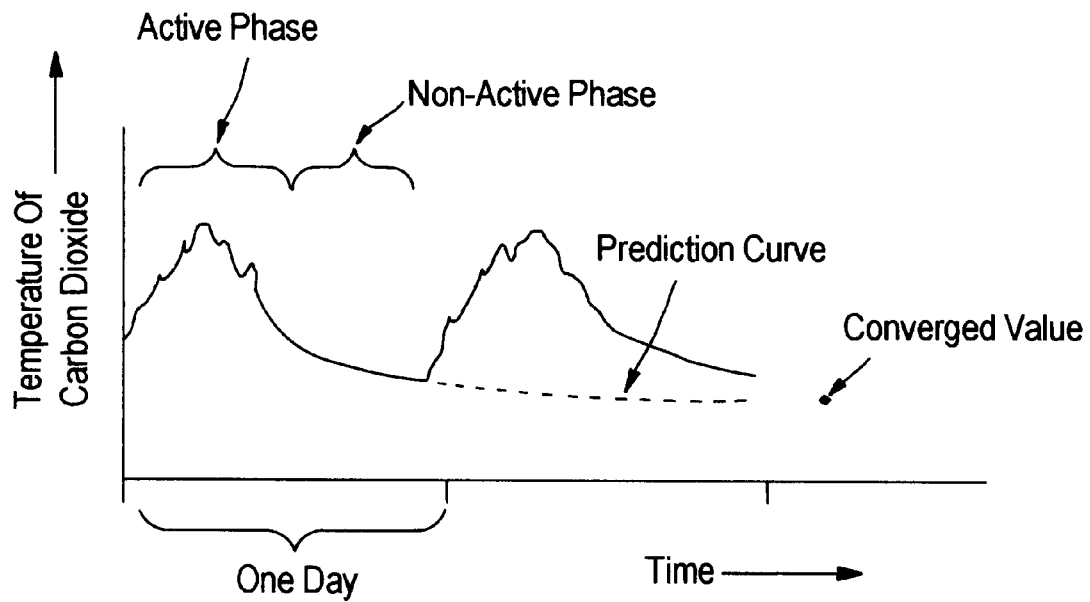
FIG. 2 graphically shows a condition in which the sensitivity correction factor is obtainable.

Now, the operation of the sensor described above will be described. FIG. 2 shows a typical example of carbon dioxide concentrations in the rooms of ordinary office buildings, schools, and other similar institutions. While varying greatly during the active period when many people come in and go out, the carbon dioxide concentration in such spaces drops in the inactive period, and converges to a certain minimum value. The arithmetic unit 12 calculates the convergence point by sensing such condition based on the preset time data and signals from the non-dispersive infrared sensor 1, and drawing a prediction curve.

How the gas concentration in the enclosed environment having a cubic volume R (m$^3$) where gas is evolved at a rate of k(m$^3$/h) can be expressed by the following general formula:

$$p = p_o + k/Q \cdot \{1 - \exp(-Q/R \cdot t)\}$$

where p=gas concentration in the enclosed environment (volume ratio)

$P_o$=gas concentration in the atmosphere (volume ratio)

Q=rate of ventilation (m$^3$/h)

t=time

When the carbon dioxide concentration in rooms of ordinary office buildings, schools and other similar institutions changes from the active phase to the non-active phase, the carbon dioxide evolution rate k and the ventilation rate Q are considered to be constant. The cubic volume of the room R is also unchanging. Therefore, $-k/Q$, $-Q/R(=b)$ and $p_o + k/Q (=\alpha)$ are all constants.

Accordingly, the damping characteristic of the carbon dioxide concentration in the non-active phase can be expressed as an exponential function of time t by the following general formula:

$$\text{Concentration } f(t) = C \cdot \exp(b \cdot t) + \alpha \qquad (1)$$

where C and b are both constants.

Here, the exponential function becomes 0 if time is infinite because b $(=-Q/R)<0$. Therefore, the concentration f(t) can be expressed as follows:

Concentration $f(t) = \alpha (t \to \infty)$

As such, $\alpha$ can be said to be an ideal minimum value.

Here, equation (1) can be re-written as $f(t) - \alpha = C \cdot \exp(b \cdot t)$ Now the right term consists of only an exponential function. Based on the exponential function's law that the rate of change in a fixed length of time is constant, the following relationship is obtainable.

$$\frac{\{f(t1)-\alpha\}-\{f(t2)-\alpha\}}{\{f(t1)-\alpha\}} = \frac{\{f(t2)-\alpha\}-\{f(t3)-\alpha\}}{\{f(t2)-\alpha\}} \quad (2)$$

where t1, t2 and t2 are consecutive time intervals. Thus, $$\alpha = \frac{\{f(t1)\}^2 - f(t1) \cdot f(t3)}{2 \cdot f(t2) - f(t1) - f(t3)} \quad (3)$$

Figure 3:
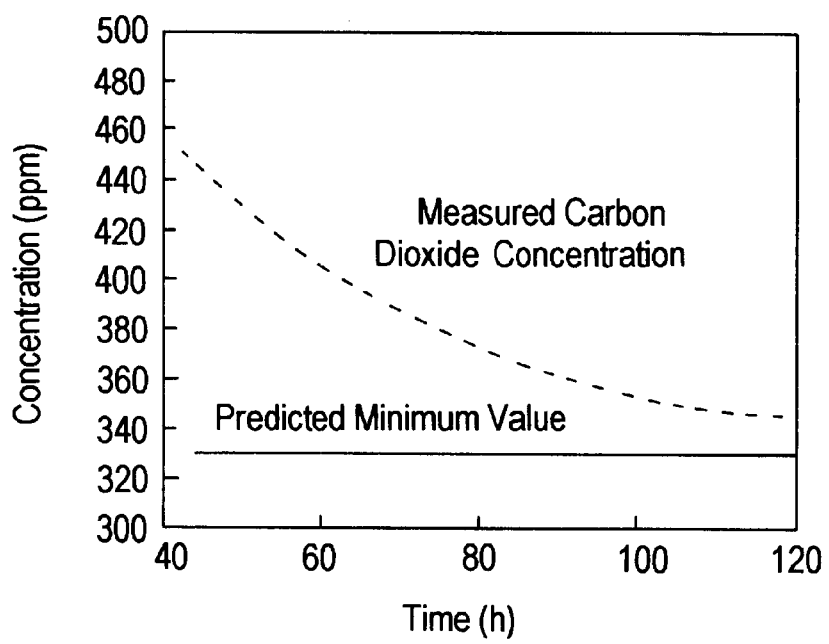
FIG. 3 graphically shows the convergent value of carbon dioxide concentration predicted by the carbon dioxide sensor of this invention.
Figure 4:
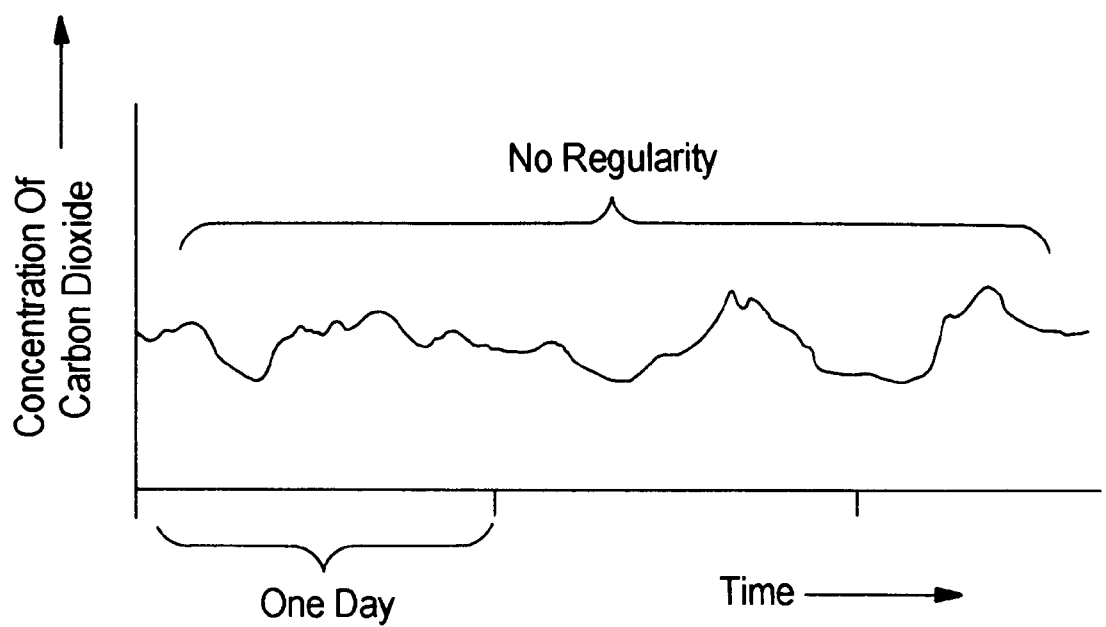
FIG. 4 graphically shows a condition in which the sensitivity correction factor is unobtainable.

By deriving the concentrations at the three consecutive points from equation (3), the converged concentration at a given point after the decreasing phase has set in, as shown in FIG. 3.

Having no relationship with the values of constants C and b, equation (3) has such a high universality that it is applicable to any environments so far as the values of the cubic volume R ($m^3$), rate of gas evolution k ($m^3$/h) and rate of ventilation Q ($m^3$/h).

When the carbon dioxide concentration in the environment changes according to the rule regulated by diffusion equation, the calibration unit 13 performs calibration by updating the sensitivity correction factor based on the calculated carbon dioxide concentration at the converging point without waiting until the actual carbon dioxide concentration reaches the minimum value.

When the carbon dioxide concentration does not exhibit a declining tendency, the arithmetic unit 12 does not make calculation to determine the converging point by judging that the environment does not permit automatic sensitivity correction and the calibration unit 13 corrects the sensitivity based on the preceding sensitivity correction factor. If the sensitivity of the non-dispersive infrared sensor 1 changes with temperature, more accurate sensitivity correction factor can be derived by implementing temperature correction based on the signals from the temperature sensor 8.

In the embodiment described above, whether the carbon dioxide concentration in the environment has come to exhibit a declining tendency that permits calibration is detected based on the preset data collected during the nighttime or holidays. The same judgement can also be made by checking changes in the signals from the carbon dioxide sensor.

Evidently, the same result can be obtained by using other types of carbon dioxide concentration sensors employing solid electrolytes or other carbon dioxide sensing means than the non-dispersive infrared sensor used in the embodiment described earlier.

The carbon dioxide concentration sensors according to this invention have an arithmetic unit that predicts the minimum value of carbon dioxide concentration that is regulated by the diffusion of the atmosphere by judging that the carbon dioxide concentration has entered a declining phase based on the signals from the carbon dioxide concentration sensing unit and a calibration unit that updates the sensitivity correction factor based on the minimum value thus predicted. Therefore, the carbon dioxide concentration sensors of this invention implement accurate calibration of time-dependent changes in the carbon dioxide sensing unit by predicting the accurate minimum value even in poorly ventilated environments, without waiting until the actual carbon dioxide concentration has dropped to the minimum value.

What is claimed is:

1. A carbon dioxide concentration sensor, comprising:
an arithmetic unit;
a carbon dioxide sensing unit having an output coupled to an input of the arithmetic unit; and
a calibration unit adapted to receive an output of the arithmetic unit and the output of the carbon dioxide sensing unit,
wherein the arithmetic unit predicts a minimum value of a carbon dioxide concentration in an environment when the carbon dioxide concentration is declining over a plurality of successive time intervals, and
wherein the calibration unit updates a sensitivity correction factor of the carbon dioxide sensing unit based on said minimum value of the carbon dioxide concentration predicted by the arithmetic unit.

2. A carbon dioxide concentration sensor according to claim 1, further comprising a memory arranged between the carbon dioxide sensing unit and the arithmetic unit,
wherein said arithmetic unit calculates a converging point of the carbon dioxide concentration by calculating a prediction curve based on a plurality of carbon dioxide concentration data points collected by said carbon dioxide sensing unit and stored in the memory.

3. A carbon dioxide concentration sensor according to claim 1, wherein said arithmetic unit calculates a converging point of the carbon dioxide concentration based on values of carbon dioxide concentration measured at each of three consecutive times spaced by one or more time intervals.

4. A carbon dioxide concentration sensor according to claim 1, wherein said arithmetic unit predicts said minimum value of the carbon dioxide concentration when a current elapsed time agrees with a preset time interval.

5. A carbon dioxide concentration sensor according to claim 1, wherein, when the carbon dioxide concentration does not exhibit a declining tendency,
said arithmetic unit does not predict the maximum value of the carbon dioxide concentration in the environment, and
said calibration unit corrects the sensitivity correction factor of the carbon dioxide sensing unit based on a preceding sensitivity correction factor.

6. A carbon dioxide concentration sensor according to claim 1, wherein said calibration unit updates the sensitivity correction factor of the carbon dioxide sensing unit so that the minimum value of the carbon dioxide concentration predicted by said arithmetic unit agrees with a reference value.

7. A method for compensating for changes in a sensitivity of a carbon dioxide concentration sensor, the method comprising:
detecting a carbon dioxide concentration in an environment during each of a plurality of consecutive time intervals;
determining a decreasing carbon dioxide concentration trend in the environment over the plurality of consecutive time intervals;
predicting a minimum carbon dioxide concentration value in the environment;
correcting at least one calibration factor of the carbon dioxide concentration sensor by using the predicted minimum carbon dioxide concentration value as a reference value if the decreasing carbon dioxide concentration trend is determined; and
outputting a calibrated carbon dioxide concentration value.

8. The method of claim 7, further comprising compensating for a temperature-dependent sensitivity of the carbon dioxide concentration sensor.

9. The method of claim 7, wherein said correcting step includes updating a sensitivity correction factor of the carbon dioxide concentration sensor.

10. The method of claim 7, wherein said correcting step includes updating a zero point of the carbon dioxide concentration sensor.

11. The method of claim 7, further comprising storing, in a memory, a plurality of carbon dioxide concentration values associated with the plurality of consecutive time intervals.

12. The method of claim 7, wherein said correcting step includes using a preceding calibration factor if the decreasing carbon dioxide concentration trend in the environment is not determined.

13. The method of claim 7, wherein said predicting step comprises:

measuring the carbon dioxide concentration at each of three consecutive times spaced by one or more time intervals; and calculating the minimum carbon dioxide concentration value by predicting a convergence point of the carbon dioxide concentration based on values of carbon dioxide concentration at said each of three consecutive times.

14. The method of claim 7, wherein said predicting step comprises fitting associated carbon dioxide concentration values at each of the plurality of consecutive time intervals to a dampened exponential curve.

15. The method of claim 14, wherein said fitting step includes converging the associated carbon dioxide concentration values to predict the minimum carbon dioxide concentration value.

16. The method of claim 7, wherein said predicting step comprises fitting associated carbon dioxide concentration values at each of the plurality of consecutive time intervals to a gas diffusion equation.

17. The method of claim 7, wherein said predicting step predicts the minimum carbon dioxide concentration value in the environment before an actual carbon dioxide concentration value decreases to the minimum carbon dioxide concentration value.

\* \* \* \* \*